United States Patent
McCusker-Orth et al.

(10) Patent No.: US 6,979,751 B2
(45) Date of Patent: Dec. 27, 2005

(54) PROCESSES FOR THE PREPARATION OF HIGHER MOLECULAR WEIGHT KETONES

(75) Inventors: Jennifer Ellen McCusker-Orth, Kingsport, TN (US); Brent Alan Tennant, Kingsport, TN (US); James Charles Ciula, Indianapolis, IN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/713,727

(22) Filed: Nov. 14, 2003

(65) Prior Publication Data

US 2004/0122261 A1 Jun. 24, 2004

Related U.S. Application Data

(60) Provisional application No. 60/436,200, filed on Dec. 23, 2002.

(51) Int. Cl.$^7$ ............................................. C07C 45/72
(52) U.S. Cl. ..................... 568/345; 568/350; 568/390; 568/396
(58) Field of Search ................................ 568/390, 396, 568/345, 350

(56) References Cited

U.S. PATENT DOCUMENTS

| | | |
|---|---|---|
| 2,088,015 A | 7/1937 | Wickert |
| 2,088,016 A | 7/1937 | Wickert |
| 2,088,017 A | 7/1937 | Wickert |
| 2,088,018 A | 7/1937 | Wickert |
| 2,200,216 A | 5/1940 | Loewenberg et al. |
| 2,485,989 A | 10/1949 | Smith |
| 2,499,172 A | 2/1950 | Smith |
| 3,666,816 A | 5/1972 | Takagi et al. |
| 4,049,571 A | 9/1977 | Nissen et al. |
| 4,146,581 A | 3/1979 | Nissen et al. |
| 4,212,825 A | 7/1980 | Nissen et al. |
| 4,239,657 A | 12/1980 | Nissen et al. |
| 4,270,006 A | 5/1981 | Heilen et al. |
| 4,694,108 A | 9/1987 | Elliott |
| 4,701,562 A | 10/1987 | Olson |
| 4,704,480 A | 11/1987 | Gefri et al. |
| 4,739,122 A | 4/1988 | Letts |
| 5,055,621 A | 10/1991 | Payne |
| 5,300,654 A | 4/1994 | Nakajima et al. |
| 5,324,871 A | 6/1994 | Carduck et al. |
| 5,583,263 A | 12/1996 | Muthusamy et al. |
| 5,663,452 A | 9/1997 | Kulmala et al. |
| 5,840,992 A | 11/1998 | Kido et al. |
| 5,955,636 A | 9/1999 | Kido et al. |
| 6,040,481 A | 3/2000 | Chambost et al. |
| 6,180,837 B1 | 1/2001 | Giffels et al. |
| 6,232,506 B1 | 5/2001 | Kido et al. |
| 6,288,288 B1 | 9/2001 | Springer |
| 6,380,437 B1 | 4/2002 | Shi et al. |
| 6,417,406 B1 | 7/2002 | Krill et al. |
| 6,433,230 B1 | 8/2002 | Bueschken et al. |
| 6,441,255 B1 | 8/2002 | Haas et al. |
| 6,448,457 B1 | 9/2002 | Hesse et al. |
| 6,603,047 B2 | 8/2003 | Wiese et al. |
| 6,605,746 B2 | 8/2003 | Krill et al. |
| 2002/0058846 A1 | 5/2002 | Krill et al. |
| 2002/0128517 A1 | 9/2002 | Krill |
| 2002/0161263 A1 | 10/2002 | Shi et al. |
| 2002/0161264 A1 | 10/2002 | Wiese et al. |
| 2002/0169342 A1 | 11/2002 | Shi et al. |
| 2002/0169347 A1 | 11/2002 | Kaizik et al. |
| 2003/0040645 A1 | 2/2003 | Krill et al. |

FOREIGN PATENT DOCUMENTS

| | | |
|---|---|---|
| EP | 0 271 182 A1 | 6/1988 |
| GB | 656405 | 8/1951 |

OTHER PUBLICATIONS

Kyrides, JACS, vol. 55, Aug. 1933, pp. 3431–3435 The Condensation of Aldehydes with ketones and some of the product derived from the ketone.

Powell, JACS, vol. 46, 1924, pp. 2514–2517 The Condensation of normal butyraldehyde with methyl ethyl ketone.

Streitwieser and Heathcock, "Introduction to Organic Chemistry", 2nd Ed., 1981, pp. 392–396.

H. O. House, Modern Synthetic Reactions, 2nd Ed., 1972, pp. 595–599, 629–640.

*Primary Examiner*—Johann Richter
*Assistant Examiner*—Sikarl A. Witherspoon
(74) *Attorney, Agent, or Firm*—Polly C. Owen; Bernard J. Graves, Jr.

(57) ABSTRACT

Processes for producing higher molecular weight ketones are disclosed that include the steps of feeding an aldol catalyst solution, a lower molecular weight aldehyde, and a lower molecular weight ketone, through a reactor provided with a solid hydrogenation catalyst and hydrogen gas; recovering a liquid reactor effluent containing the higher molecular weight ketone as a reaction product; and recycling a portion of the recovered liquid reactor effluent back through the reactor.

76 Claims, No Drawings

PROCESSES FOR THE PREPARATION OF HIGHER MOLECULAR WEIGHT KETONES

CROSS REFERENCE TO RELATED APPLICATIONS

This application claims benefit of priority under 35 USC § 119(e) to U.S. Provisional Application No. 60/436,200, filed on Dec. 23, 2002, the contents of which are incorporated herein by reference.

FIELD OF THE INVENTION

This invention relates generally to the production of ketones, and more specifically, to processes for producing higher molecular weight ketones that result in higher yields and greater selectivity for the target product, while minimizing the formation of by-products that are difficult to remove from the reaction mixture via distillation.

BACKGROUND OF THE INVENTION

Aldol condensation reactions are important in the production of intermediates needed to synthesize many commercially important products. The condensation of ketones to obtain aldols (β-hydroxy ketones) is a well-known reaction. Dehydration of the resulting aldol to obtain an unsaturated ketone is also known. Subsequent catalytic hydrogenation of the unsaturated ketone may be carried out to obtain the corresponding saturated higher ketone.

In an aldol condensation reaction, two aldehydes or ketones, or one of each, each having a hydrogen atom alpha to the carbonyl, react together to form a β-hydroxy-aldehyde or a β-hydroxy-ketone. Many methods have been disclosed in the art to perform aldol condensation reactions. These include two-phase liquid reactions using dilute aqueous base as the catalyst, see, for example, U.S. Pat. No. 6,232,506, U.S. Pat. Appln. No. 2002/0161264, U.S. Pat. No. 6,433,230, U.S. Pat. No. 2,200,216, U.S. Pat. No. 6,288,288; base-catalyzed, liquid phase aldol condensation reactions that include the use of a solubilizing or phase transfer agent, see, for example, U.S. Pat. Nos. 2,088,015, 2,088,016, 2,088,017, and 2,088,018; and the use of polymeric or oligomeric ethylene glycols or polyhydric alcohols as phase transfer catalysts or solvents in combination with dilute alkali metal hydroxide catalysts, see, for example, U.S. Pat. Nos. 5,055,621, and 5,663,452, and U.S. Pat. Publ. No.2002/0058846.

The β-hydroxy-aldehyde or β-hydroxy-ketone product of such aldol condensations can dehydrate to give a conjugated α,β-unsaturated aldehyde or ketone. Many methods are known in the art for dehydrating β-hydroxy-aldehydes or β-hydroxy-ketones to α,β-unsaturated aldehydes or ketones, in fair to excellent yields. These include simple heating; acid-catalyzed dehydration using mineral acids or solid acid catalysts, with or without azeotropic removal of the water of reaction, as exemplified in U.S. Pat. No. 5,583,263, U.S. Pat. No. 5,840,992, U.S. Pat. No. 5,300,654, and Kyrides, JACS, Vol 55, August, 1933, pp. 3431–3435; heating with iodine crystals, as in Powell, JACS, Vol. 46, 1924, pp. 2514–17; and base-catalyzed dehydration, as taught in Streitwieser and Heathcock, "Introduction to Organic Chemistry", $2^{nd}$ Ed., 1981, pp. 392–396.

The conditions needed for the aldol dehydration are often only a bit more vigorous than the conditions needed for the aldol condensation itself. As a result, the α,β-unsaturated ketone is often the only product obtained from the reaction, while the initial β-hydroxy ketone is not typically isolated.

In some cases, it is desirable to selectively hydrogenate the carbon-carbon double bond of the resulting α,β-unsaturated ketone to give a saturated ketone. Many catalysts and methods are known for such hydrogenation reactions, as exemplified in U.S. Pat. Nos. 5,583,263 and 5,840,992, and U.S. Pat. Appl. Nos. 2002/0128517, 2002/058846, and 2002/0169347. Alkenes react with hydrogen gas in the presence of a suitable metal catalyst, typically palladium or platinum, to yield the corresponding saturated alkane addition products. The metal catalysts are normally employed on a support or inert material, such as carbon or alumina. Commercially important products of this type include methyl amyl ketone, methyl isoamyl ketone, and methyl propyl ketone, made by the crossed condensation of acetone with n-butyraldehyde, isobutyraldehyde, or acetaldehyde, respectively.

Aldehydes are more reactive, in general, than are ketones in base-catalyzed aldol condensations, because of the greater ease of enolate ion formation of an aldehyde. As such, in a crossed condensation of a ketone with an aldehyde to produce a desired β-hydroxyketone, the self-condensation of the aldehyde typically occurs in substantial quantities to produce an undesired β-hydroxyaldehyde by-product. Further, unhindered aldehydes, i.e., straight-chain aldehydes such as acetaldehyde, propionaldehyde, n-butyraldehyde, and n-pentanal, are more reactive toward self-condensation than hindered aldehydes, i.e., branched aldehydes such as 2-methyl-propanal and 3-methyl-butanal.

It is understood that the rate-limiting step in these reactions is often the enolate ion formation, and that condensation and the subsequent dehydration reaction occur in rapid succession. These α-β unsaturated ketones and aldehydes are known to those skilled in the art to be quite reactive and susceptible to further consecutive, non-selective condensation, cyclization, and Michael-type addition reactions with the starting ketones and aldehydes, as well as themselves and other ketonic and aldehydic by-products. See, for example, H. O. House, Modern Synthetic Reactions, $2^{nd}$. Ed., 1972 pp. 595–599, 629–640.

Thus, in the base-catalyzed crossed condensation of an aldehyde of Formula I, possessing at least one hydrogen atom alpha to the carbonyl, with a ketone of Formula II, to form a desired β-hydroxy-ketone or α-β unsaturated ketone of Formulae III or IV, three parallel reaction pathways are known to compete:

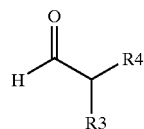

Formula I

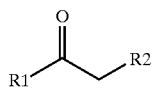

Formula II

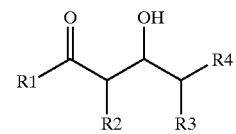

b-hydroxy-ketone of Formula III

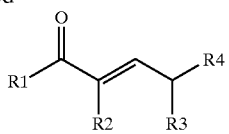

a-b unsaturated ketone of Formula IV

-continued

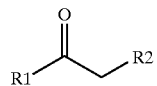

+

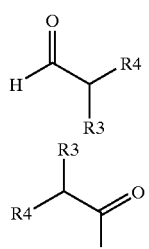

→ 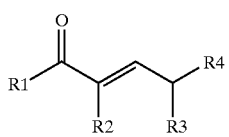 −H₂O→ 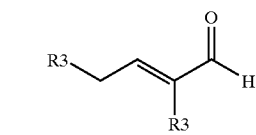 → Further Condensation Products

+

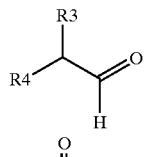

→ (see structure) −H₂O→ (see structure) → Further Condensation Products

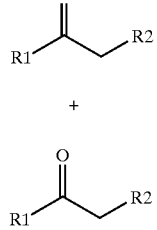

+

(acetone-type)

⇌ (see structure) ⇌−H₂O 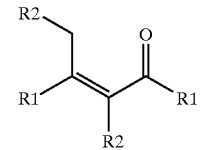 → Further condensation Products

In general, R2, R1, R3, and R4 represent hydrogen or a C1 to C10 organic radical.

One skilled in the art would expect a broad range of products from these reactions. The further condensation of the α-β unsaturated ketones with the ketone of Formula II, or with the aldehyde of Formula I, or with other ketonic and aldehydic species, leads to many by-products and can represent significant yield losses as well as necessitate complicated and expensive purification schemes for the commercial production of high purity α,β-unsaturated ketones and saturated ketones. For example, in the preparation of methyl amyl ketone via the crossed condensation of n-butyraldehyde with acetone, the self-condensation of n-butyraldehyde to form 2-ethyl-2-hexenal is a particularly troublesome by-product. Its hydrogenated form, 2-ethylhexanal, boils less than 10° C. apart from 2-heptanone, and is therefore difficult to separate economically from 2-heptanone by distillation. It would clearly be an advance in the art to minimize formation of these unwanted aldehyde self-condensation by-products that are afterward difficult to remove from the reaction mixture.

One method of preventing unwanted further condensation side products in aldol condensation reactions is to quickly hydrogenate the α,β-unsaturated ketones. This can be accomplished in situ or in a separate hydrogenation step.

The production of higher molecular weight ketones using aldol condensations and catalytic hydrogenations can be carried out either by a multi-step process or a one-step process. A multi-step process uses sequentially discrete steps in two or three separate reactors. In a one-step process the reactions are carried out simultaneously in one reactor.

When ketones are synthesized by a multi-step process, using sequentially discrete steps, the aldol reaction occurs first, which is then followed by dehydration, and by subsequent hydrogenation. Each step is independent of the others, and the process often requires difficult separation techniques between steps. For example, U.S. Pat. No. 5,583,263 describes a multi-step process for the coproduction of methyl amyl ketone and methyl isobutyl ketone. In this process, dimethyl ketone is reacted with n-butyraldehyde using a fixed-bed basic ion exchange cross-aldol condensation catalyst to form a β-hydroxy ketone mixture. The product is then dehydrated to form an olefinic ketone using a catalytic quantity of an acidic substance, such as $H_2SO_4$, $NaHSO_4$, or a sulfonic acid resin. The resulting α,β-unsaturated ketone is then hydrogenated using a solid phase hydrogenation catalyst to produce the desired amyl ketone. Three discrete steps are required, with costly separations between the steps. There is no acknowledgment that by-products other than methyl isobutyl ketone are produced, nor is there any suggestion how one might avoid impurities such as 2-ethylhexaldehyde and high boiling by-products that result from unwanted side reactions. On the basis of a comparative example, the authors conclude that commercial coproduction of methyl isobutyl ketone and methyl amyl ketone is impractical in one-step processes employing ordinary catalyst systems.

When ketones are produced in a one-step process, the aldol reaction, dehydration, and hydrogenation occur simultaneously in one reactor. Such one-step processes can be either batch or continuous processes.

In a one-step batch process, the reactions are carried out simultaneously in one reactor, and there is neither inflow nor outflow of reactants or products while the reaction is being carried out. In a one-step continuous process, the reactions are carried out simultaneously in one reactor, and reactants flow in and the products flow out while the reaction is being carried out. While the hydrogenation reaction is typically heterogeneously catalyzed, the aldol condensation can be either heterogeneously or homogeneously catalyzed in a one-step process.

For example, U.S. Pat. No. 2,499,172 (the '172 patent) describes a one-step batch process for the conversion of low-boiling ketones to high boiling ketones. Higher boiling ketones, such as methyl isobutyl ketone, are produced when lower boiling ketones, such as acetone and ethyl methyl ketone, are treated with hydrogen in the presence of a liquid alkaline condensation catalyst and a solid hydrogenation catalyst. The liquid alkaline condensation catalyst can be ammonia; amines, such as isopropylamine, diisopropylamine, trimethylamine, furfurylamine, difurfurylamine, and aniline; alkali-metal hydroxides; alkaline-earth-metal oxides and hydroxides; and alkali-metal salts of weak acids, such as sodium borate, carbonate, acetate and phosphates. The solid hydrogenation catalyst can contain palladium, for example 5% Pd/C.

The examples of the '172 patent describe a one-step batch process for the self-condensation of ketones. In general, self-aldol condensations of ketones lead to only one product. For example, the self-aldol condensation and hydrogenation product of dimethylketone is methyl isobutyl ketone. However, crossed aldol condensations—between ketones and aldehydes—lead to mixtures of products. For example, the crossed aldol condensation and hydrogenaton products of dimethylketone and n-butyraldehye are methyl amyl ketone, methyl isobutyl ketone, and 2-ethylhexaldehyde. We have found that when the one-step batch process described in the '172 patent is applied to the crossed aldol condensation of acetone and n-butyraldehdye, as seen in Example 1 (Comparative) of the present application, a large amount of high-boiling material is produced. As a result, the selectivity of n-butyraldehyde to methyl amyl ketone is poor. A further disadvantage of batch processes in general is that they often require large reaction apparatuses and storage tanks, because their capacity relative to the reaction volume is very small. Other drawbacks include high energy consumption and operator involvement, and high conversion costs.

The '172 patent advises that the process described in that patent may be carried out by passing the reactant mixture through a stationary bed of pelleted or supported catalysts, enclosed in a reaction vessel of suitable design. This suggests a fixed-bed plug-flow reactor process, such as that described in U.S. Pat. No. 5,324,871 for the hydrogenation of fatty acids and fatty acid esters to fatty alcohols, where the reactants are pumped straight through the catalyst bed and continually consumed as they flow down the length of a reactor, such as a tubular reactor. A fixed-bed reactor, sometimes called a packed-bed reactor, is typically a tubular reactor that is packed with solid catalyst particles.

When a continuous, fixed-bed plug-flow concept is applied to the crossed aldol condensation of acetone and n-butyraldehyde without recycle, as seen in Example 2 (Comparative) of the present application, a large amount of 2-ethylhexaldehyde by-product is produced, the result of the self-aldol condensation of n-butyraldehyde. The selectivity of n-butyraldehyde to methyl amyl ketone is thus very low, only 38%. While the use of a continuous plug-flow fixed-bed catalyst helps eliminate some of the disadvantages of a one-step batch process, such as the difficult catalyst recovery operations typical of a slurry process, we have not found this alternative to improve conversion or selectivity in crossed aldol condensation reactions. The main by-product of the one-step batch process, unknown high-boilers, can be easily separated from methyl amyl ketone. However, the main by-product of the continuous plug-flow fixed-bed catalyst process, 2-ethylhexaldehyde, cannot be easily separated from the methyl amyl ketone by distillation.

There remains a need for an improved process for producing higher molecular weight ketones having a higher yield and greater selectivity for the target product, which minimizes the amounts of unwanted by-products that are afterward difficult to remove from the reaction mixture.

SUMMARY OF THE INVENTION

The present invention relates to processes for producing higher molecular weight ketones, that include the steps of feeding an aldol catalyst solution, a lower molecular weight aldehyde, and a lower molecular weight ketone, through a reactor provided with a solid hydrogenation catalyst and hydrogen gas; recovering a liquid reactor effluent containing the higher molecular weight ketone as a reaction product; and recycling a portion of the recovered liquid reactor effluent back through the reactor. In one embodiment, the recycle ratio of the volume of liquid reactor effluent recycled back through the reactor, with respect to the volume of the portion of the liquid reactor effluent that is not recycled, is from about 1 to 1 to about 1000 to 1. That portion of the liquid reactor effluent that is not recycled may be fed to a second reactor, may be otherwise further reacted in one or more additional reactions, or may be removed from further reaction and the desired higher molecular weight ketone isolated. The second reactor may be of substantially the same form as, and function in substantially the same way as, the first reactor, or may differ from the first reactor in one or more respects.

DETAILED DESCRIPTION OF THE INVENTION

The present invention may be understood more readily by reference to the following detailed description of the invention, and to the Examples included therein.

Before the present compositions of matter and methods are disclosed and described, it is to be understood that this invention is not limited to specific synthetic methods or to particular formulations, unless otherwise indicated, and, as such, may vary from the disclosure. It is also to be understood that the terminology used is for the purpose of describing particular embodiments only, and is not intended to limit the scope of the invention.

The singular forms "a," "an," and "the" include plural referents, unless the context clearly dictates otherwise.

Optional or optionally means that the subsequently described event or circumstances may or may not occur. The description includes instances where the event or circumstance occurs, and instances where it does not occur.

Ranges may be expressed herein as from about one particular value, and/or to about another particular value. When such a range is expressed, it is to be understood that another embodiment is from the one particular value and/or to the other particular value.

Throughout this application, where patents or publications are referenced, the disclosures of these references in their entireties are intended to be incorporated by reference into this application, in order to more fully describe the state of the art to which the invention pertains.

The present invention relates to processes for producing higher molecular weight ketones. The processes according to the invention allow the three reaction steps of condensation, dehydration, and hydrogenation to occur simultaneously in a tubular reactor. According to the invention, though not wishing to be bound by any theory, a ketone and an aldehyde are condensed together using an aldol catalyst solution, provided for example as a liquid base in an aqueous catalyst phase. The resulting aldol is dehydrated by the liquid base to yield an unsaturated ketone. This olefinic species is then hydrogenated over a solid hydrogenation catalyst provided in the reactor, which may be a tubular fixed-bed reactor provided with a metal catalyst on a support material.

The higher molecular weight ketones produced according to the invention are those having molecular weights that are higher than the molecular weights of the ketones and aldehydes used as reactants. It follows that the lower molecular weight aldehydes and ketones used as reactants according to the invention have molecular weights that are lower than those of the higher molecular weight ketone products that they are used to produce.

We have unexpectedly discovered that recycling a portion of the reaction mixture just described back to the reactor drastically affects yield and selectivity. The recycle ratio, as used herein, is defined as the ratio of the volume of the liquid reactor effluent recycled, with respect to the volume of the liquid reactor effluent that is not recycled. In the process according to the invention, there will also be a gaseous reactor effluent exiting the reactor, the volume of which may vary, for example, based on the pressure of the hydrogen gas provided to the reactor. This gaseous reactor effluent is not measured for purposes of determining the recycle ratio. The portion of the liquid reactor effluent that is not recycled back through the reactor may be used directly in one or more additional reactions, such as by being fed to a second reactor, or may be removed from further reaction and the desired higher molecular weight ketone isolated.

With a recycle ratio from about 1 to 1 to about 1000 to 1, much less aldehyde self-condensation product is produced than with a continuous plug-flow process, higher yields and selectivity for the target higher molecular weight ketone are achieved, lesser amounts of low- and high-boilers are produced, and the impurity profile is improved. While we expect that recycle ratios in excess of 1000 to 1 would result in similarly satisfactory performance, the recycle flow rate that would be required to obtain such a recycle ratio would be quite high.

In other embodiments, the process is carried out using a recycle ratio of at least about 1 to 1, or at least about 2 to 1, or at least about 3 to 1. The invention may also be carried out within a range of recycle ratios from about 1 to 1 to about 500 to 1, or from about 1 to 1 to about 100 to 1.

The recycle used according to the invention provides higher molecular weight ketones, with high conversion and good selectivity, while being a simpler and more economical process than many conventional methods. By using recycle, as further described below; we have been able to achieve both higher conversion and improved selectivity. Furthermore, the process according to the invention may be carried out in one or more tubular or fixed-bed trickle reactors used in series, avoiding the use of stirred tank reactors and other more complex reaction schemes.

The reaction mixture present in the reactor includes an aldol catalyst solution, which may be an aqueous solution, an aldehyde reactant, and a ketone reactant. The reaction mixture may also contain additional material, such as an alcohol, though such additional materials are not preferred, due to later problems in separation. The reaction may therefore be carried out in the presence of, or in the absence of, one or more alcohols that are added to the reaction mixture.

In one embodiment, the process according to the invention involves continously feeding two liquid phases (an organic reactant phase and an aldol catalyst phase) over a solid phase (a hydrogenation catalyst fixed in a trickle bed reactor), under hydrogen pressure, while continously removing product formed by removing a portion of the liquid reactor effluent exiting the reactor from the reactor system, while recycling the remainder back through the reactor.

Recycling a portion of the product stream, as disclosed for example in U.S. Pat. No. 6,448,457 related to a method of hydrogenating carbonyl compounds, is a process by which a portion of a reaction mixture exiting a reactor is returned back to the reactor, rather than being removed from further reaction such as by removal from the reactor system. Modest recycle is typically used to recover expensive catalysts or unreacted starting materials. In addition, it can be used to control process variables, such as temperature. U.S. Pat. No. 6,040,481, related to a method for hydrogenating aromatic nitro compounds, describes another example of recycling a portion of a reaction mixture exiting a reactor.

In general, lower molecular weight aldehydes having from 2 to 20 carbon atoms are useful as reactants according to the invention, and especially aliphatic aldehydes having from 2 to 6 carbon atoms. These aldehydes may be straight-chain alkyls, or may be branched, or may be an aldehyde corresponding to Formula I below:

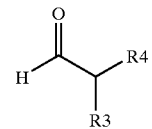

Aldehyde of Formula 1 wherein R3, and R4 may each independently represent hydrogen, or else R3 and R4 form members of a common alicyclic ring of 4 to 15 carbon atoms, preferably from 4 to 8 carbon atoms, and especially 5 to 6 carbon atoms, such as a cyclohexyl radical, which alicyclic ring may be substituted with one or more branched or unbranched, saturated or unsaturated aliphatic or alkyl-substituted cycloaliphatic, or aromatic hydrocarbon radicals of 1 to 15 carbon atoms, preferably 1 to 12 carbon atoms, or with halogens or ether functionalities; or else R3 or R4 may represent a branched or unbranched, saturated or unsaturated aliphatic or alkyl-substituted cycloaliphatic hydrocarbon radical of 1 to 15 carbon atoms, preferably from 1 to 12 carbon atoms, and especially from 1 to 6 carbon atoms, such as a methyl, ethyl, n-propyl, or n-butyl radical, which aliphatic or cycloaliphatic hydrocarbon radical may be substituted with halogens or ether functionalities; or R3 or R4 may represent a saturated or unsaturated alkyl-substituted cycloaliphatic hydrocarbon radical of 3 to 12 carbon atoms, preferably from 3 to 8 carbon atoms, and especially from 5 to 6 carbon atoms, which cycloaliphatic hydrocarbon radical may contain alkyl groups as substituents, or which may be substituted with halogens or ether functionalities; or else R3 or R4 may represent an aryl hydrocarbon radical of 6 to 15 carbon atoms, preferably from 6 to 9 carbon atoms, and especially a phenyl radical, which aryl hydrocarbon radical may be substituted with halogens or ether functionalities; or else R3 or R4 may represent an alkylaryl hydrocarbon radical of 7 to 15 carbon atoms, preferably from 7 to 10 carbon atoms, and especially a benzyl radical, which alkylaryl hydrocarbon radical may be substituted with halogens or ether functionalities.

In a similar embodiment, R3 and R4 may each represent hydrogen, may represent a substituted or unsubstituted, straight or branched chain aliphatic radical containing 1 to 20 carbon atoms; a substituted or unsubstituted, straight or branched chain alkenyl radical containing 2 to 20 carbon atoms; a substituted or unsubstituted cycloalkyl or cycloalkenyl radical containing 4 to 20 carbon atoms; a substituted or unsubstituted aryl radical containing 6 to 20 carbon atoms, e.g., phenyl or napthyl; or a substituted or unsubstituted 4- to 20-membered heterocylic radical containing from 1 to 3 heteroatoms selected from oxygen and sulfur. The term "heterocyclic radical" denotes optionally substituted four to ten-membered rings that have 1 to 3 heteroatoms, selected independently from oxygen and sulfur. These four- to ten-membered rings may be saturated, partially unsaturated, or fully unsaturated.

The term "substituted" as used herein in conjunction with each of the alkyl, alkenyl, cycloalkyl, cycloalkenyl, aryl, and heterocyclic radicals which may be represented by R1, R2, R3, and R4 denotes the above radicals substituted with one or more halogen, $C_1$–$C_6$-alkyl, $C_1$–$C_6$-alkoxy, substituted $C_1$–$C_6$-alkyl, $C_1$–$C_6$-alkylthio, aryl, arylthio, aryloxy, $C_2$–$C_6$-alkoxycarbonyl, $C_2$–$C_6$-alkanoylamino, hydroxy, carboxyl, cycloalkoxy, nitro, keto, thioether, aldehydo, carboalkoxy, imido, sulfinato, sulfanato, sulfonamide, sulfoxy, phosphato, cycloalkyl, amino, mono-substituted amino, di-substituted amino, acyloxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkoxy, acyloxy, acyl, alkyl, alkoxy, aminoacyl, acylamino, azido, carboxylalkyl, cyano, heteroaryl, heteroaryloxy, heterocyclyl, heterocylooxy, aminoacyloxy, oxyacylamino, thioalkoxy, substituted thioalkoxy, thioaryloxy, thioheteroaryloxy, trihalomethyl, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, or arylcarbonylamino groups.

Examples of substituted and unsubstituted alkyl and alkenyl radicals include, but are not limited to, methyl, ethyl, cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl, n-propyl, isopropyl, isobutyl, n-butyl, tertiary butyl, pentyl, hexyl, 2-ethylhexyl, octyl, decyl, vinyl, 1-propenyl, 1-butenyl, 1-pentenyl, 2-octenyl, and various isomers thereof.

Examples of substituted and unsubstituted cycloalkyl and cycloalkenyl radicals include, but are not limited to, cyclopropyl, cyclobutyl, hydroxymethyl-cyclobutyl, cyclobutenyl, cyclopentyl, cyclopentenyl, cyclohexyl, cyclohexyl-carbonyloxy, cyclohexenyl, cycloheptyl, 2-methylcyclopropyl, cycloheptenyl, 4-methylcyclohexyl, 3-methylcyclopentenyl, 4-(isopropyl)-cyclohexylethyl or 2-methyl-cyclopropylpentyl, and the like. Examples of heterocyclic radicals are tetrahydrofuranyl, tetrahydrothiofuranyl, thienyl, dioxanyl, pyranyl, furyl, chromenyl, xanthenyl, phenoxathiinyl, oxepane, oxathiolanyl, benzothienyl, and the like. Examples of substituted and unsubstituted aryl radicals are 4-chlorophenyl, 2,6-dichlorophenyl, 2,5-dichlorophenyl, 3,4-dichlorophenyl, 3-chlorophenyl, 3-bromophenyl, 4-bromoindenyl, 3,4-dibromophenyl, 3,4-dibromonaphthyl, 3-chloro-4-fluorophenyl, 2-fluorophenyl and the like; a mono- or di(hydroxy)aryl radical such as 4-hydroxyphenyl, 3-hydroxyphenyl, 2,4-dihydroxyphenyl, and the like; a nitroaryl group such as 3- or 4-nitrophenyl; a cyanoaryl group, for example, 4-cyanophenyl; a mono- or di(lower alkyl)aryl radical such as 4-methylphenyl, 2,4-dimethylphenyl, 2-methylnaphthyl, 4-(iso-propyl)phenyl, 4-ethylnaphthyl, 3-(n-propyl)phenyl and the like; a mono- or di(alkoxy)aryl radical, for example, 2,6-dimethoxyphenyl, 4-methoxyphenyl, 3-ethoxyindenyl, 4-(iso-propoxy)phenyl, 4-(t-butoxy)phenyl, 3-ethoxy-4-methoxyphenyl and the like; 3- or 4-trifluoro-methylphenyl, a mono- or dicarboxyaryl radical such as 4-carboxyphenyl, 4-carboxynaphthyl; a mono- or di(hydroxymethyl)aryl radical such as 3,4-di(hydroxymethyl)phenyl, a mono- or di(aminomethyl)aryl radical such as 2-(aminomethyl)phenyl, or a mono- or di(methylsulfonylamino)aryl radical such as 3-(methylsulfonylamino)naphthyl.

Specific examples of aldehydes useful as reactants according to the invention include, but are not limited to, acetaldehyde; propionaldehyde; n-butyraldehyde; 2-methylpropanal; n-pentanal and structural isomers such as 2-methyl-butanal, 3-methyl-butanal, 2,2-dimethyl-propanal; n-hexanal and structural isomers such as 2-ethyl-butanal, 2,2-dimethylbutanal, 2,3-dimethylbutanal, 2-methylpentanal, 3-methylpentanal, 4-methyl-pentanal; n-heptanal and structural isomers such as 2-methylhexanal, 2-ethylpentanal, 2,2-dimethylpentanal, 2,3-dimethylpentanal, 2,4-dimethylpentanal, 2-ethyl-3-methylbutanal, 2-ethyl-2-methylbutanal; n-octanal and structural isomers such as 2-ethylhexanal, n-nonanal and structural isomers; cyclopropane carboxaldehyde; cyclobutane carboxaldehyde; cyclopentane carboxaldehyde; cyclohexane carboxaldehyde; 2-methylcyclohexane carboxaldehyde; 3-methylhexane carboxaldehyde; and 4-methylhexane carboxaldehyde.

Similarly, lower molecular weight ketones having from 3 to 20 carbon atoms are useful according to the invention, and especially aliphatic ketones. These ketones may be straight-chain alkyls, or may be branched, or may be any ketone corresponding to Formula 2 below:

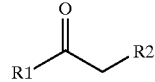

Ketone of Formula 2

R1 is an unbranched or branched alkyl of 1 to 20 carbon atoms, preferably of 1 to 8 carbon atoms, and especially of 1 to 5 carbon atoms, aryl or cycloalkyl which are unsubstituted or substituted by lower alkyl, preferably phenyl or cyclohexyl, or aralkyl of 7 to 20 carbon atoms, preferably of 7 to 10 carbon atoms, R2 represents hydrogen or an unbranched or branched alkyl of 1 to 20 carbon atoms, preferably of 1 to 8 carbon atoms, and especially of 1 to 5 carbon atoms, aryl or cycloalkyl which are unsubstituted or substituted by lower alkyl, preferably phenyl or cyclohexyl, or aralkyl of 7 to 20 carbon atoms, preferably of 7 to 10 carbon atoms.

Or R2 represents hydrogen, or else R1 and R2 form members of a common alicyclic ring of 4 to 8 carbon atoms, preferably 5 to 6 carbon atoms, which alicyclic ring may be substituted with one or more branched or unbranched, saturated or unsaturated aliphatic or alkyl-substituted cycloaliphatic, or aromatic hydrocarbon radicals of 1 to 20 carbon atoms, preferably 1 to 12 carbon atoms, or with halogens or ether functionalities;

or else R1 represents a branched or unbranched, saturated or unsaturated aliphatic or alkyl-substituted cycloaliphatic hydrocarbon radical of 1 to 20 carbon atoms, preferably from 1 to 12 carbon atoms, or from 1 to 4 carbon atoms, and especially a methyl, ethyl, n-butyl, t-butyl, or i-butyl radical, which aliphatic or alkyl-substituted cycloaliphatic hydrocarbon radical may be substituted with halogens or ether functionalities; or else R1 represents a saturated or unsaturated alkyl-substituted cycloaliphatic hydrocarbon radical of 3 to 12 carbon atoms, preferably 3 to 8 carbon atoms, and especially 5 to 6 carbon atoms, which cycloaliphatic hydrocarbon radical may contain alkyl groups as substituents, and which may be substituted with halogens or ether functionalities; or else R1 represents an aryl hydrocarbon radical of 6 to 15 carbon atoms, preferably 6 to 9 carbon atoms, and especially a phenyl radical, which aryl hydrocarbon radical may be substituted with halogens or ether functionalities; or else R1 represents an alkylaryl hydrocarbon radical of 7 to 15 carbon atoms, preferably 7 to 10 carbon atoms, and especially a benzyl radical, which alkylaryl hydrocarbon radical may be substituted with halogens or ether functionalities.

In a similar embodiment, R2 may represent hydrogen, or R1 and R2 each represent a substituted or unsubstituted, straight or branched chain aliphatic radical containing 1 to 10 carbon atoms; a substituted or unsubstituted, straight or branched chain alkenyl radical containing 2 to 10 carbon atoms; a substituted or unsubstituted cycloalkyl or cycloalkenyl radical containing 4 to 10 carbon atoms; a substituted or unsubstituted aryl radical containing 6 to 10 carbon atoms, e.g., phenyl or napthyl; or a substituted or unsubstituted 4- to 10-membered heterocylic radical containing from 1 to 3 heteroatoms selected from oxygen and sulfur. The term "heterocyclic radical" denotes optionally substituted four to ten-membered rings that have 1 to 3 heteroatoms, selected independently from oxygen and sulfur. These four- to ten-membered rings may be saturated, partially unsaturated, or fully unsaturated. For the present process, it is preferred that R2 is methyl, phenyl, or vinyl; however, it is especially preferred that R2 is hydrogen.

Specific examples of ketones useful as reactants according to the invention include, but are not limited to, acetone, 2-butanone, 2-pentanone, and 3-methyl-2-butanone. Preferred ketones are methyl ketones, most preferably acetone and methyl ethyl ketone.

The molar ratio of ketone reactant to aldehyde reactant in the reaction can be varied over a wide range. In order to minimize aldehyde self-condensation products, a molar excess of ketone is preferred. However, to avoid the recycle of unnecessarily large amounts of unreacted ketone and water/organic separation problems, in general, from about 1 to about 20 moles of ketone can be used per mole of aldehyde, or from about 2 to about 10 moles of ketone per mole of aldehyde, or from about 2 to about 5 moles of ketone per mole of aldehyde.

Liquid bases provided as the aldol catalyst, that are suitable for use as catalysts for the aldol condensation reaction and the dehydration reaction, include solutions of the hydroxides or alkoxides of alkali-metals or alkaline-earth metals. These catalysts include, but are not limited to, sodium hydroxide, potassium hydroxide, cesium hydroxide, lithium hydroxide, magnesium hydroxide, calcium hydroxide, barium hydroxide, sodium methoxide, sodium ethoxide, sodium propoxide, sodium butoxide, potassium methoxide, potassium ethoxide, potassium propoxide, potassium butoxide, cesium methoxide, cesium ethoxide, cesium propoxide, cesium butoxide, lithium methoxide, lithium ethoxide, lithium propoxide, lithium butoxide, magnesium methoxide, magnesium ethoxide, magnesium propoxide, magnesium butoxide, calcium methoxide, calcium ethoxide, calcium propoxide, calcium butoxide, barium methoxide, barium ethoxide, barium propoxide, barium butoxide. Preferably, sodium hydroxide or potassium hydroxide are used because they are readily available and inexpensive.

The amount of the aldol catalyst (such as a base) to be added can vary within wide limits. However, it has been found that from about 0.001 to about 0.4 equivalents, or from about 0.005 to about 0.2 equivalents of base, or from about 0.05 to 0.15 about equivalents, relative to the molar amount of aldehyde, are useful ranges. They are preferably used in dissolved form.

The concentration of catalyst, or base, useful according to the invention can vary, and may be provided as an aqueous solution, such as from about 0.5 wt % to about 50 wt %, or from about 0.5 wt % to about 25 wt %, or from about 2 to about 10 wt %.

The processes according to the invention may be carried out in one or more fixed-bed reactors, such as tubular reactors packed with solid catalyst particles. These fixed-bed reactors may be the same as, or different from, one another. Fixed-bed reactor systems are typically more economical than slurry powder catalyst systems, which require gravity settling, filtration, centrifugation, and pumping of the catalyst. Catalyst slurry pumps are subject to high mechanical wear, and the quantitative removal of the powder catalysts from the reaction product is often complicated. With a fixed-bed reactor system, the need for catalyst recovery is thereby eliminated.

The solid hydrogenation catalysts of these reactors may be shaped or extruded transition metal catalysts, wherein the transition metal is typically supported on a stable support, sometimes described as an "inert" stable support. Preferred hydrogenation catalysts include, but are not limited to, transition metal catalyst systems having active components comprised of Ni, Co, Cu, or Cr; noble metal catalyst systems having active components comprised of Pt, Pd, Rh, Ru, Re, or Ir; and combinations of these catalysts. Suitable supports include, but are not limited to, alumina, silica, a combination of alumina and silica, denoted as silica-alumina, and carbon. Pd on C is a preferred solid hydrogenation catalyst.

The metal weight loadings of the solid hydrogenation catalysts useful according to the invention may vary within a wide range, from about 0.1 to about 90 wt. %, or even greater. It is generally understood that catalytic activity is controlled by the exposed transition metal surface area of such catalysts. Therefore, the desired weight loadings of catalysts in this process will be governed by the activity desired in the fixed-bed process. A preferred metal weight loading is from about 0.1 to about 5.0 wt. %.

The processes according to the invention may be carried out by passing the aldehyde and ketone reactant mixture, and the aldol catalyst solution, through a stationary bed of pelleted or supported hydrogenation catalysts, enclosed in a tubular reactor. This is typical of continuous fixed-bed plug-flow reactor processes, where the reactants are continually consumed as they flow down the length of the reactor. However, as seen in Example 2 (Comparative), when this continuous plug-flow fixed-bed concept is applied to the cross-aldol condensation of acetone and n-butyraldehyde, the selectivity of n-butyraldehyde to methyl amyl ketone is very low, only 38%. The main-by-product, 2-ethylhexaldehyde, the result of the self-aldol condensation of n-butyraldehyde, cannot be easily separated from the methyl amyl ketone by distillation.

In the processes according to the invention, the conversion achieved in the plug-flow reactor is improved greatly by recycling a portion of the product stream so that it returns to the entrance of the reactor for an additional pass through the reactor. Recycle is thus the process by which a portion of the reaction mixture, which may contain unconsumed reactants or by-products, is returned back to the reactor, rather than being removed from further reaction, for example by removal from the reactor system, or by being fed into one or more additional reactors. Modest recycle is typically used to recover expensive catalysts or unreacted starting materials. In addition, it can be used to control process variables, such as temperature. The rate at which the material is removed from the reactor to again flow back through the reactor is called the recycle rate. The recycle ratio is defined as the volume of the fluid exiting the reactor that is returned to the reactor, divided by the volume exiting the reactor that is not returned to the reaction, and may be removed from further reaction by being removed from the reactor system, or may be fed to one or more additional reactors, as the case may be. Thus, in contrast to conventional plug-flow processes, the process according to the invention is conducted such that only a portion of the reactor effluent from one pass through the fixed bed is removed; the remainder is recycled back to the reactor.

The reactor temperature can be chosen in general within a wide range, i.e., from about 0° C. to about 200° C. Lower temperatures result in incomplete conversions and often require longer residence times in the reactor, which result in the production of unwanted high boiling impurities. Higher temperatures, which yield higher conversions, also result in unwanted high boiling impurities as well as increase the probability for over-hydrogenation. In other embodiments, the reaction temperature is between 25° C. and 175° C., or between 50° C. and 165° C., or between 90° and 130° C.

The reaction pressure of the hydrogen gas provided in the reactor, chosen to optimize conversion and selectivity, is generally from about 3 to about 150 bar. Sufficient hydrogenation of the alkene must be carefully balanced against over-hydrogenation of the carbonyl group to an alcohol. In various embodiments, the pressure is from about 6 to about 75 bar, or from about 10 to about 40 bar, or from about 15 to about 30 bar.

Residence time is the average length of time the reactants spend in the reactor. Thus the residence time is the amount of material in the reactor (the volume of the reactor), divided by either the inflow or the outflow, which are equal when the system is at equilibrium. A wide range of residence times can be employed according to the invention, generally from about 2 to about 200 minutes. The residence time chosen, while chosen to optimize both conversion and selectivity, will be related to the hydrogenation catalyst chosen and is somewhat dependent on temperature. More active hydrogenation catalysts will require less residence time. Thus, the residence time may be from about 2 to about 200 minutes, or from about 10 to about 100 minutes, or from about 20 to about 60 minutes.

In a preferred embodiment according to the invention, one or more fixed bed reactors are used in series. The fixed-beds can be identical or different, depending on the desired conversion and selectivity. The fixed beds can be different sizes, packed with different catalysts, different catalyst loadings, conducted under different temperatures and pressures, or can be substantially the same. When two fixed beds are used in series, an even higher conversion of intermediates (such as 3-heptene-2-one to MAK) is obtained, higher yields and selectivity for the target ketone (of n-butyraldehyde to MAK) are achieved, and lower amounts of unwanted by-products that are difficult to separate by distillation are obtained, such as 2-ethylhexaldehyde, when compared with a process using a single fixed bed reactor. As seen, for example, in examples 24 and 25, the yield and selectivity of n-butyraldehyde for MAK increases substantially with the use of two beds, rather than just one. In addition, the amount of 2-ethylhexaldehyde is reduced by nearly half. In a preferred embodiment, two fixed bed reactors are used, in combination with recycle.

This invention can be further illustrated by the following examples of preferred embodiments thereof, although it will be understood that these examples are included merely for purposes of illustration and are not intended to limit the scope of the invention unless otherwise specifically indicated.

EXAMPLES

For the examples and comparative examples described herein, unless otherwise noted, conversion and selectivity terms are defined as follows:

$$\% \text{ Conversion of n-butyraldehyde} = \frac{\text{moles n-butyraldehyde reacted}}{\text{moles n-butyraldehyde in feed}}$$

$$\% \text{ Selectivity} = \frac{\text{moles Methyl Amyl Ketone formed}}{\text{moles n-butyraldehyde reacted}}$$

All analyses were done by gas chromatography using a Hewlett-Packard model 5890 gas chromatograph, equipped with a DB-5 column, TC detector, and auto injector. For each analysis, the initial temperature of the column was set at 35° C., held for 2 minutes, and ramped to 250° C. at a rate of 20° C. per minute, and held for 2 to 5 minutes at 250° C.

Example 1 (Comparative)

Batch Slurry Production of Methyl Amyl Ketone 70.25 grams of acetone, 26.84 grams of n-butyraldehyde, 1.35 grams of 1% Pd/C catalyst (Engelhard CG-31, available from Engelhard Corporation, Iselin, N.J.), and 45 mL of 3-wt % sodium hydroxide were charged to a 300 ml autoclave fitted with a magnetic stirrer, nitrogen purge, cooling coil, and temperature-controlled heater. The autoclave was sealed, purged with nitrogen, pressurized to 20 bar of hydrogen, and heated to 100° C. After stirring the mixture for 1 hour at 100° C., the solution was cooled and the pressure was released. The product samples were analyzed, as were all the samples of the application, by capillary GLC analysis.

TABLE 1

Results from Example 1 (Comparative)

| MAK Product Composition From: | Batch Slurry Reactor |
|---|---|
| Water | 6.39 |
| Acetone | 26.9 |
| n-butyraldehyde | 0.03 |
| Methyl Isobutyl ketone | 3.22 |
| Methyl Amyl Ketone | 28.2 |
| 3-heptene-2-one | 0.008 |
| 2-ethyl-hexaldehyde | 1.1 |
| High and low boilers | 27.71 |
| n-butyraldehyde conversion | 99.93 |
| Selectivity | 41.09 |

As can be seen from the results in Table 1, when a one-step batch process is used for the cross-aldol condensation of acetone and n-butyraldehdye, a large amount, 27.71%, of unknown high-boiling material is produced. In addition, the selectivity of n-butyraldehyde to methyl amyl ketone is poor, 41.09%.

Example 2 (Comparative)

Continuous Plug-Flow Fixed-Bed Production of Methyl Amyl Ketone (Without Recycle)

The experiment was carried out in a continuous mode of operation using as a reactor a vertical pressure vessel having a length of 72 inches and an inside diameter of 1 inch. Temperature measurements in the reactor were made with a series of 10 thermocouples inserted into the wall of the reactor. The reactor system held approximately 1 L of liquid material. The reactor was loaded with 772 mL of a 0.5% Pd/C catalyst (Engelhard CBA-300, available from Engelhard Corporation, Iselin, N.J.). The catalyst was positioned above and supported by 104 mL of Pro-PAK packing (available from Aldrich, Milwaukee, Wis.). An additional 150 mL of Pro-PAK packing was placed on top of the catalyst.

The feed reservoirs were jacketed, 4-L graduated vessels with a bottom take-off valve. A 3-wt % caustic solution was pumped into the reactor at a rate of 300 mL/hr. The organic solution, a mixture of acetone and n-butyraldehyde (2.5:1 molar ratio), was pumped into the system at 1000 mL/hr. The system pressure was 25 bar and the temperature was 90° C.

The organic/aqueous feed mixture was fed at the top of the reactor vessel along with hydrogen. Crude product was removed from the bottom of the reactor and fed to a level pot to separate the hydrogen from the crude product. From the level pot, the crude product was removed from the MAK production system. After the system reached the desired process settings (temperature, pressure, and feed rate), the system was held at equilibrium for the appropriate amount of time (3 full bed turnovers). The product samples were analyzed by capillary GLC analysis. Results can be found in Table 2

Examples 3–6

Continuous Fixed-Bed Production of Methyl Amyl Ketone (With Recycle)

The experiments of Examples 3–6 were carried out in a continuous mode of operation using as a reactor a vertical pressure vessel having a length of 72 inches and an inside diameter of 1 inch. Temperature measurements in the reactor were made with a series of 10 thermocouples inserted into the wall of the reactor. The reactor system held approximately 1 L of liquid material. The reactor was loaded with 772 mL of a 0.5% Pd/C catalyst (Engelhard CBA-300). The catalyst was positioned above and supported by 104 mL of Pro-PAK packing. An additional 150 mL of Pro-PAK packing was placed on top of the catalyst. The feed reservoirs were jacketed, 4-L graduated vessels with a bottom take-off valve. A 3-wt % caustic solution was pumped into the reactor at a rate of 300 mL/hr. The organic solution, a mixture of acetone and n-butyraldehyde (2.5:1 molar ratio), was pumped into the system at 1000 mL/hr. The system pressure was 25 bar and the temperature was 90° C. For Examples 3, 4, 5, and 6 the liquid was recycled through the system at recycle rates of 10, 20, 30 and 40 L/hr, respectively.

The organic/aqueous recycle feed mixture was fed at the top of the reactor vessel along with hydrogen. Crude product was removed from the bottom of the reactor and fed to a level pot to separate the hydrogen from the crude product. From the level pot, a portion of the crude product was removed from the MAK production system and the remainder recycled. After the system reached the desired process settings (temperature, pressure, feed rate, and recycle rate), the system was held at equilibrium for the appropriate amount of time (3 full bed turnovers). The product samples were analyzed by capillary GLC analysis.

TABLE 2

Results from Examples 2, 3, 4, 5, and 6

| MAK Product Composition From: | Example 2 Plug Flow | Example 3 With 10 L/hr Recycle | Example 4 With 20 L/hr Recycle | Example 5 With 30 L/hr Recycle | Example 6 With 40 L/hr Recycle |
|---|---|---|---|---|---|
| Recycle Ratio | 0 | 7.6 | 15 | 23 | 30 |
| Water | 8.78 | 9.94 | 9.63 | 9.59 | 9.48 |
| Acetone | 29.7 | 22.12 | 20.4 | 19.9 | 18.2 |
| n-butyraldehyde | 0.11 | 0.55 | 0.24 | 0.49 | 0.35 |
| Methyl Isobutyl Ketone | 0.23 | 0.58 | 0.56 | 0.58 | 0.52 |
| Methyl Amyl Ketone | 27.01 | 41.62 | 44.28 | 45.11 | 46.1 |
| 3-heptene-2-one | 1.01 | 1.34 | 1.17 | 1.4 | 1.39 |
| 2-ethyl-hexaldehyde | 11.03 | 1.81 | 1.617 | 0.977 | 0.90 |
| High and low boilers | 11.32 | 4.84 | 3.86 | 4.48 | 4.11 |
| n-butyraldehyde conversion | 99.74 | 98.68 | 99.43 | 98.83 | 99.18 |
| Selectivity | 38.4 | 62.97 | 66.00 | 67.91 | 68.2 |

As can be seen in the results from Table 2, increasing the recycle ratio gives higher selectivity to Methyl Amyl Ketone and lower levels of 2-ethyl-hexaldehyde. With no recycle, or a plug-flow process, the level of 2-ethyl-hexaldehyde under the same process conditions was 11.03% while selectivity was only 38.4%.

Examples 7–12

Continuous Fixed-Bed Production of Methyl Amyl Ketone (With Recycle)

The experiments of Examples 7–12 were carried out in a continuous mode of operation using as a reactor a vertical pressure vessel having a length of 72 inches and an inside diameter of 1 inch. Temperature measurements in the reactor were made with a series of 10 thermocouples inserted into the wall of the reactor. The reactor system held approximately 1 L of liquid material. The reactor was loaded with 96 mL of a 0.5% Pd/C catalyst (Engelhard CBA-300). The catalyst was positioned above and supported by 450 mL of Pro-PAK packing. An additional 450 mL of Pro-PAK packing was placed on top of the catalyst. The feed reservoirs were jacketed, 4-L graduated vessels with a bottom take-off valve. A 3-wt % caustic solution was pumped into the reactor at a rate of 125 mL/hr. The organic solution, a mixture of acetone and n-butyraldehyde (3.25:1 molar ratio), was pumped into the system at 312 mL/hr. The system pressure was 20 bar and the temperature was 115° C. For Examples 7, 8, 9, 10, 11, and 12 the liquid was recycled through the system at recycle rates of 4, 8, 13, 22 and 42 L/hr, respectively.

The organic/aqueous recycle feed mixture was fed at the top of the reactor vessel along with hydrogen. Crude product was removed from the bottom of the reactor and fed to a level pot to separate the hydrogen from the crude product. From the level pot, a portion of the crude product was removed from the MAK production system and the remainder recycled. After the system reached the desired process settings (temperature, pressure, feed rate, and recycle rate), the system was held at equilibrium for the appropriate amount of time (3 full bed turnovers). The product samples were analyzed by capillary GLC analysis. Results can be found in Table 3.

As can be seen in the results from Table 3, increasing the recycle ratio gives lower levels of 2-ethyl-hexaldehyde. At a recycle ratio of 10 the 2-EHA level in 0.12%, while at a recycle ratio of 100, the 2-EHA level is 0.04%.

Example 13 (Comparative)

Continuous Plug-Flow Fixed-Bed Production of Methyl Amyl Ketone (Without Recycle)

The experiment was carried out in a continuous mode of operation using as a reactor a vertical pressure vessel having a length of 72 inches and an inside diameter of 1 inch. Temperature measurements in the reactor were made with a series of 10 thermocouples inserted into the wall of the reactor. The reactor system held approximately 1 L of liquid material. The reactor was loaded with 193 mL of a 0.5% Pd/C catalyst (Engelhard CBA-300). The catalyst was positioned above and supported by 400 mL of Pro-PAK packing. An additional 400 mL of Pro-PAK packing was placed on top of the catalyst. The feed reservoirs were jacketed, 4-L graduated vessels with a bottom take-off valve. A 3-wt % caustic solution was pumped into the reactor at a rate of 250 mL/hr. The organic solution, a mixture of acetone and n-butyraldehyde (3.25:1 molar ratio), was pumped into the system at 625 mL/hr. The system pressure was 20 bar and the temperature was 115° C.

The organic/aqueous feed mixture was fed at the top of the reactor vessel along with hydrogen. Crude product was removed from the bottom of the reactor and fed to a level pot to separate the hydrogen from the crude product. From the level pot, the crude product was removed from the MAK production system. After the system reached the desired process settings (temperature, pressure, and feed rate), the system was held at equilibrium for the appropriate amount of time (3 full bed turnovers). The product samples were analyzed by capillary GLC analysis. Results can be found in Table 4.

Examples 14–20

Continuous Fixed-Bed Production of Methyl Amyl Ketone (With Recycle)

The experiments of Examples 14–20 were carried out in a continuous mode of operation using as a reactor a vertical pressure vessel having a length of 72 inches and an inside

TABLE 3

Results from Examples 7, 8, 9, 10, 11, 12

| MAK Product Composition From: | Example 7 With 4 L/hr Recycle | Example 8 With 8 L/hr Recycle | Example 9 With 13 L/hr Recycle | Example 10 With 22 L/hr Recycle | Example 11 With 33 L/hr Recycle | Example 12 With 42 L/hr Recycle |
|---|---|---|---|---|---|---|
| Recycle Ratio | 10 | 20 | 30 | 50 | 75 | 100 |
| Water | 4.94 | 4.8 | 5.27 | 5.07 | 4.73 | 4.90 |
| Acetone | 23.90 | 23.62 | 23.32 | 22.02 | 21.96 | 22.88 |
| n-butyraldehyde | 0.06 | 0.07 | 0.07 | 0.07 | 0.07 | 0.07 |
| Methyl Isobutyl Ketone | 3.99 | 4.19 | 5.79 | 5.51 | 5.28 | 4.85 |
| Methyl Amyl Ketone | 33.22 | 34.4 | 43.78 | 45.17 | 43.59 | 40.49 |
| 3-heptene-2-one | 3.69 | 4.01 | 2.36 | 3.01 | 3.60 | 3.87 |
| 2-ethyl-hexaldehyde | 0.12 | 0.09 | 0.08 | 0.06 | 0.05 | 0.04 |
| High and low boilers | 23.73 | 23.09 | 13.95 | 13.95 | 15.82 | 18.04 |
| n-butyraldehyde conversion | 99.86 | 99.83 | 99.82 | 99.84 | 99.82 | 99.83 |
| Selectivity | 48.69 | 50.10 | 67.76 | 67.83 | 64.36 | 60.03 | diameter of 1 inch. Temperature measurements in the reactor were made with a series of 10 thermocouples inserted into the wall of the reactor. The reactor system held approximately 1 L of liquid material. The reactor was loaded with 193 mL of a 0.5% Pd/C catalyst (Engelhard CBA-300). The catalyst was positioned above and supported by 400 mL of Pro-PAK packing. An additional 400 mL of Pro-PAK packing was placed on top of the catalyst. The feed reservoirs were jacketed, 4-L graduated vessels with a bottom take-off valve. A 3-wt % caustic solution was pumped into the reactor at a rate of 250 mL/hr. The organic solution, a mixture of acetone and n-butyraldehyde (3.25:1 molar ratio), was pumped into the system at 625 mL/hr. The system pressure was 20 bar and the temperature was 115° C. For Examples 14, 15, 16, 17, 18, 19, and 20 the liquid was recycled through the system at recycle rates of 0.8, 1.7, 4.3, 9, 17.5, 26.5, and 42 L/hr, respectively.

The organic/aqueous recycle feed mixture was fed at the top of the reactor vessel along with hydrogen. Crude product was removed from the bottom of the reactor and fed to a level pot to separate the hydrogen from the crude product. From the level pot, a portion of the crude product was removed from the MAK production system and the remainder recycled. After the system reached the desired process settings (temperature, pressure, feed rate, and recycle rate), the system was held at equilibrium for the appropriate amount of time (3 full bed turnovers). The product samples were analyzed by capillary GLC analysis. Results can be found in Table 4.

The catalyst was positioned above and supported by 104 mL of Pro-PAK packing. An additional 150 mL of Pro-PAK packing was placed on top of the catalyst.

The feed reservoirs were jacketed, 4-L graduated vessels with a bottom take-off valve. A 3-wt % caustic solution was pumped into the reactor at rates of 900, 600, and 300 mL/hr, in Examples 6, 7, and 8, respectively. The organic solution, a mixture of acetone and n-butyraldehyde (2.5:1 molar ratio) was pumped into the system at feed rates of 3,000, 2,000, and 1,000 mL/hr, respectively. The system pressure was 20 bar and the temperature was 100° C. The organic/aqueous recycle feed mixture was fed at the top of the reactor vessel along with hydrogen.

Crude product was removed from the bottom of the reactor and fed to a level pot to separate the hydrogen from the crude product. From the level pot, a portion of the crude product was removed from the MAK production system and the remainder recycled at 35 L/hr. After the system reached the desired process settings (temperature, pressure, feed rate, and recycle rate), the system was held at equilibrium for the appropriate amount of time (3 full bed turnovers). The product samples were analyzed by capillary GLC analysis. Results can be found in Table 5.

TABLE 4

| MAK Product Composition From: | Example 13 Plug Flow | Example 14 With 0.8 L/hr Recycle | Example 15 With 1.7 L/hr Recycle | Example 16 With 4.3 L/hr Recycle | Example 17 With 9 L/hr Recycle | Example 18 With 17.5 L/hr Recycle | Example 19 With 26.5 L/hr Recycle | Example 20 With 42 L/hr Recycle |
|---|---|---|---|---|---|---|---|---|
| Recycle Ratio | 0 | 1 | 2 | 5 | 10 | 20 | 30 | 40 |
| Water | 4.26 | 5.48 | 5.20 | 5.85 | 5.50 | 5.67 | 5.61 | 5.60 |
| Acetone | 21.38 | 23.94 | 22.99 | 23.99 | 23.51 | 24.03 | 23.95 | 23.64 |
| n-butyraldehyde | 0.00 | 0.02 | 0.03 | 0.05 | 0.07 | 0.05 | 0.05 | 0.05 |
| Methyl Isobutyl Ketone | 3.38 | 3.94 | 4.26 | 4.37 | 4.69 | 4.50 | 4.44 | 4.76 |
| Methyl Amyl Ketone | 12.35 | 32.87 | 34.82 | 41.88 | 45.68 | 43.84 | 44.81 | 43.78 |
| 3-heptene-2-one | 0.06 | 0.86 | 0.94 | 1.58 | 1.92 | 3.02 | 3.30 | 3.51 |
| 2-ethyl-hexaldehyde | 1.16 | 0.63 | 0.58 | 0.38 | 0.29 | 0.16 | 0.11 | 0.08 |
| High and low boilers | 52.60 | 26.52 | 25.34 | 15.95 | 12.29 | 13.44 | 12.45 | 13.18 |
| n-butyraldehyde conversion | 100.00 | 99.96 | 99.93 | 99.88 | 99.84 | 99.88 | 99.87 | 99.87 |
| Selectivity | 16.28 | 48.12 | 50.54 | 64.14 | 70.29 | 67.92 | 69.18 | 67.61 |

As can be seen in the results from Table 4, increasing the recycle ratio gives higher selectivity to Methyl Amyl Ketone, lower levels of 2-ethyl-hexaldehyde, and lower levels of high and low boilers. With no recycle, or a plug-flow process, the level of high and low boilers under the same process conditions was 52.60% while selectivity was only 16.28%.

Examples 21–23

Continuous Fixed-Bed Production of Methyl Amyl Ketone (With Recycle)

The experiments of Examples 21 through 23 were carried out in a continuous mode of operation using as a reactor a vertical pressure vessel having a length of 72 inches and an inside diameter of 1 inch. The reactor system held approximately 1 L of liquid material. Temperature measurements in the reactor were made with a series of 10 thermocouples inserted into the wall of the reactor. The reactor was loaded with 772 mL of a 0.5% Pd/C catalyst (Engelhard CBA-300).

TABLE 5

| MAK Product Composition From: | Example 21 | Example 22 | Example 23 |
|---|---|---|---|
| Organic Feed Rate | 3000 | 2000 | 1000 |
| Caustic Feed Rate | 900 | 600 | 300 |
| Recycle Ratio | 9 | 13 | 27 |
| Water | 7.5 | 7.91 | 8.64 |
| Acetone | 26.3 | 25.15 | 19.52 |
| n-butyraldehyde | 1.19 | 1.133 | 0.643 |
| Methyl Isobutyl Ketone | 0.35 | 0.363 | 0.527 |
| Methyl Amyl Ketone | 43.7 | 45.79 | 48.02 |
| 3-heptene-2-one | 4.36 | 2.563 | 1.48 |
| 2-ethyl-hexaldehyde | 2.41 | 2.31 | 1.287 |
| High and low boilers | 5.88 | 4.117 | 4.218 |
| n-butyraldehyde conversion | 97.2 | 97.37 | 98.53 |
| Selectivity | 64.3 | 67.27 | 69.48 |

As can be seen in the results from Table 5, increasing recycle ratio increases selectivity, as well as conversion. In addition, the level of 2-ethyl-hexaldehyde decreased with increasing recycle ratio.

Examples 24 and 25

Continuous Fixed-bed Process for the Production of Methyl Amyl Ketone Using One and Two Fixed Bed Reactors, Respectively The experiment of Example 24 was carried out in a continuous mode of operation, using as the reaction vessel a vertical pressure vessel having a length of 72 inches and an inside diameter of 1 inch. The reactor system held approximately 1 L of liquid material. Temperature measurements in the reactor were made with a series of 10 thermocouples inserted into the wall of the reactor. The reactor was loaded with 386 mL of a 0.5% Pd/C catalyst (Engelhard CBA-300). The catalyst was positioned above and supported by 390 mL of Pro-PAK packing. An additional 300 mL of the Pro-PAK packing was placed on top of the catalyst.

The feed reservoirs were jacketed, 4-L graduated vessels with a bottom take-off valve. A 3-wt % caustic solution was pumped into the reactor at a rate of 500 mL/hr. The organic solution, a mixture of acetone and n-butyraldehyde (3.2:1 molar ratio), was pumped into the system at 1250 mL/hr. The system pressure was 17 bar and the temperature was 115° C.

The organic/aqueous recycle feed mixture was fed at the top of the reactor vessel along with hydrogen. Crude product was removed from the bottom of the reactor and fed to a level pot in which hydrogen was separated from the crude product. From the level pot, a portion of the crude product was removed from the MAK production system and the remainder recycled at 30 L/hr. After the system reached the desired process settings (temperature, pressure, feed rate, and recycle rate), the system was held at equilibrium for the appropriate amount of time (3 full bed turnovers). The product samples were analyzed by capillary GLC analysis.

For Example 25, the product produced above in Example 24, using a single fixed-bed reactor, was passed through a second fixed-bed reactor. This was carried out in a continuous mode of operation using as the reaction vessel a vertical pressure vessel having a length of 72 inches and an inside diameter of 1 inch. The reactor system held approximately 1 L of liquid material. Temperature measurements in the reactor were made with a series of 10 thermocouples inserted into the wall of the reactor. The reactor was loaded with 200 mL of a 0.1% Pd/C catalyst (Engelhard CBA-300). The catalyst was positioned above and supported by 580 mL of the Pro-PAK packing. An additional 300 mL of the Pro-PAK packing was placed on top of the catalyst.

The feed reservoirs were jacketed, 4-L graduated vessels with a bottom take-off valve. The caustic solution was pumped into the reactor at a rate of 280 mL/hr. As the organic solution, the reaction product of Example 24 was pumped into the system at a rate of 700 mL/hr. The system pressure was 17 bar and the temperature was 125° C. The liquid was recycled through the system at a rate of 15 L/hr. The organic/aqueous recycle feed mixture was fed at the top of the reactor vessel along with hydrogen.

Crude product was removed from the bottom of the reactor and fed to a level pot to separate the hydrogen from the crude product. From the level pot, a portion of the crude product was removed from the MAK production system and the remainder recycled at 15 L/hr. After the system reached the desired process settings (temperature, pressure, feed rate, and recycle rate), the system was held at equilibrium for the appropriate amount of time (3 full bed turnovers). The product samples were analyzed by capillary GLC analysis. Results can be found in Table 6.

TABLE 6

| MAK Product Composition From: | Example 24 One Fixed Bed | Example 25 Two Fixed Beds |
| --- | --- | --- |
| Recycle Ratio | 17 | 15 |
| Water | 5.97 | 4.66 |
| Acetone | 28.25 | 25.45 |
| n-butyraldehyde | 0.05 | 0.02 |
| Methyl Isobutyl Ketone | 0.72 | 2.42 |
| Methyl Amyl Ketone | 41.75 | 49.8 |
| 3-heptene-2-one | 7.44 | 1.64 |
| 2-ethyl-hexaldehyde | 0.51 | 0.28 |
| High and low boilers | 10.84 | 13.44 |
| n-butyraldehyde conversion | 99.78 | 99.95 |
| Selectivity | 62.92 | 72.81 |

As can be seen in the results from Table 6, the addition of a second fixed bed reactor allows for higher selectivity to methyl amyl ketone. In addition, the levels of 3-heptene-2-one and 2-ethylhexaldhyde decrease.

Examples 26 and 27

Continuous Fixed-bed Process for the Production of Methyl Isoamyl Ketone Using One and Two Fixed Bed Reactors, Respectively The experiment of Example 26 was carried out in a continuous mode of operation, using as the reactor a vertical pressure vessel having a length of 72 inches and an inside diameter of 1 inch. The reactor system held approximately 1 L of liquid material. Temperature measurements in the reactor were made with a series of 10 thermocouples inserted into the wall of the reactor. The reactor was loaded with 386 mL of a 0.5% Pd/C catalyst (Engelhard CBA-300). The catalyst was positioned above and supported by 390 mL of Pro PAK packing. An additional 300 mL of the Pro PAK Packing was placed on top of the catalyst.

The feed reservoirs were jacketed, 4-L graduated vessels with a bottom take-off valve. A 3-wt % caustic solution was pumped into the reactor at a rate of 400 mL/hr. The organic solution, a mixture of acetone and i-butyraldehyde (3.25:1 molar ratio), was pumped into the system at 1000 mL/hr. The system pressure was 24 bar and the temperature was 140° C. The liquid was recycled through the system at the relatively high rate of 30 L/hr.

The organic/aqueous recycle feed mixture was fed at the top of the reactor vessel along with hydrogen. Crude product was removed from the bottom of the reactor and fed to a level pot to separate the hydrogen from the crude product. A portion of the crude product was collected from the MIAK production system and the remainder recycled. After the system reached the desired process settings (temperature, pressure, feed rate, and recycle rate), the system was held at equilibrium for the appropriate amount of time (3 full bed turnovers).

The product samples were analyzed by capillary GLC analysis.

In Example 27, the product produced above according to Example 26, using a single fixed-bed reactor, was then passed through a second fixed-bed reactor. This was carried out in a continuous mode of operation using as the reactor a vertical pressure vessel having a length of 72 inches and an inside diameter of 1 inch. The reactor system held approximately 1 L of liquid material. Temperature measurements in the reactor were made with a series of 10 thermocouples inserted into the wall of the reactor. The reactor was loaded with 200 mL of a 0.1% Pd/C catalyst (Engelhard CBA-300). The catalyst was positioned above and supported by 580 mL of the PRO PAK packing. An additional 300 mL of PRO PAK Packing was placed on top of the catalyst. The feed reservoirs were jacketed, 4-L graduated vessels with a bottom take-off valve. The caustic solution was pumped into the reactor at a rate of 280 mL/hr. As the organic solution, the reaction product produced in Example 26 was pumped into the system at 700 mL/hr. The system pressure was 17 bar and the temperature was 125° C. The liquid was recycled through the system at a rate of 15 L/hr. The organic/aqueous recycle feed mixture was fed at the top of the reactor vessel along with hydrogen. Crude product was removed from the bottom of the reactor and fed to a level pot to separate the hydrogen from the crude product. A portion of the crude product was collected from the MIAK production system and the remainder recycled. After the system reached the desired process settings (temperature, pressure, feed rate, and recycle rate), the system was held at equilibrium for the appropriate amount of time (3 full bed turnovers). The product samples were analyzed by capillary GLC analysis. Results can be found in Table 7.

TABLE 7

| MIAK Product Composition From: | Example 26 One Fixed Bed | Example 27 Two Fixed Beds |
|---|---|---|
| Recycle Ratio | 21 | 15 |
| Water | 4.96 | 4.587 |
| Acetone | 25.34 | 25.66 |
| i-butyraldehyde | 0.23 | 0.01 |
| Methyl Isobutyl Ketone | 4.14 | 5.64 |
| Methyl IsoAmyl Ketone | 50.51 | 54.45 |
| 5-methyl-3-hexene-2-one | 7.00 | 1.87 |
| High and low boilers | 4.19 | 3.126 |
| i-butyraldehyde conversion | 99.44 | 99.95 |
| Selectivity | 77.21 | 85.26 |

Examples 28 and 29

Continuous Fixed-bed Process for the Production of Methyl Propyl Ketone Using One and Two Fixed Bed Reactors, Respectively The experiment of Example 28 was carried out in a continuous mode of operation using as the reactor a vertical pressure vessel having a length of 72 inches and an inside diameter of 1 inch. The reactor system held approximately 1 L of liquid material. Temperature measurements in the reactor were made with a series of 10 thermocouples inserted into the wall of the reactor. The reactor was loaded with 386 mL of a 0.5% Pd/C catalyst (Engelhard CBA-300). The catalyst was positioned above and supported by 390 mL of PRO PAK packing. An additional 300 mL of the PRO PAK Packing was placed on top of the catalyst.

The feed reservoirs were jacketed, 4-L graduated vessels with a bottom take-off valve. A 3-wt % caustic solution was pumped into the reactor at a rate of 400 mL/hr. The organic solution, a mixture of acetone and acetaldehyde (3:1 molar ratio), was pumped into the system at 1100 mL/hr. The system pressure was 17 bar and the temperature was 90° C. The liquid was recycled through the system at the relatively high rate of 30 L/hr.

The organic/aqueous recycle feed mixture was fed at the top of the reactor vessel along with hydrogen. Crude product was removed from the bottom of the reactor and fed to a level pot wherein hydrogen was separated from the crude product. A portion of the crude product was collected from the MPK production system and the remainder recycled. After the system reached the desired process settings (temperature, pressure, feed rate, and recycle rate), the system was held at equilibrium for the appropriate amount of time (3 full bed turnovers). The product samples were analyzed by capillary GLC analysis.

In Example 29, the product produced above according to Example 28, using a single fixed-bed reactor, was then passed through a second fixed-bed reactor. This was carried out in a continuous mode of operation, using as the reactor a vertical pressure vessel having a length of 72 inches and an inside diameter of 1 inch. The reactor system held approximately 1 L of liquid material. Temperature measurements in the reactor were made with a series of 10 thermocouples inserted into the wall of the reactor. The reactor was loaded with 200 mL of a 0.1% Pd/C catalyst (Engelhard CBA-300). The catalyst was positioned above and supported by 580 mL of the PRO PAK packing. An additional 300 mL of the PRO PAK Packing was placed on top of the catalyst.

The feed reservoirs were jacketed, 4-L graduated vessels with a bottom take-off valve. The caustic solution was pumped into the reactor at a rate of 280 mL/hr. The organic solution reaction product produced in Example 28 was pumped into the system at 1600 mL/hr. The system pressure was 17 bar and the temperature was 110° C. The liquid was recycled through the system at a rate of 15 L/hr. The organic/aqueous recycle feed mixture was fed at the top of the reactor vessel along with hydrogen. Crude product was removed from the bottom of the reactor and fed to a level pot to separate the hydrogen from the crude product. A portion of the crude product was collected from the MPK production system and the remainder recycled. After the system reached the desired process settings (temperature, pressure, feed rate, and recycle rate), the system was held at equilibrium for the appropriate amount of time (3 full bed turnovers). The product samples were analyzed by capillary GLC analysis.

TABLE 8

| MPK Product Composition From: | Example 28 One Fixed Bed | Example 29 Two Fixed Beds |
|---|---|---|
| Recycle Ratio | 20 | 8.3 |
| Water | 18.46 | 15.11 |
| Acetone | 37.10 | 36.33 |
| Acetaldehyde | 0.14 | 0.03 |
| Methyl Isobutyl Ketone | 0.44 | 5.64 |
| Methyl Propyl Ketone | 27.65 | 30.76 |
| 3-pentene-2-one | 0.55 | 0.13 |
| C7s | 3.15 | 3.78 |
| High and low boilers | 10.29 | 9.81 |
| Acetaldehyde conversion | 99.90 | 99.88 |
| Selectivity | 27.18 | 29.08 |

The invention has been described in detail with reference to specific embodiments. It will be understood that variations and modifications can be made without departing from the scope and spirit of the invention.

We claim:

1. A process for producing a higher molecular weight ketone, comprising:

feeding an aldol catalyst solution, a lower molecular weight aldehyde, and a lower molecular weight ketone, through a reactor provided with a solid hydrogenation catalyst and hydrogen gas;

recovering a liquid reactor effluent containing the higher molecular weight ketone as a reaction product; and recycling a portion of the recovered liquid reactor effluent back through the reactor wherein the recycling is carried out at a recycle ratio of the volume of liquid reactor effluent recycled back through the reactor, with respect to the volume of the portion of the liquid reactor effluent that is not recycled, of at least about 1 to 1.

2. The process according to claim 1, wherein the recycling is carried out at a recycle ratio of the volume of liquid reactor effluent recycled back through the reactor, with respect to the volume of the portion of the liquid reactor effluent that is not recycled, from about 1 to 1 to about 1000 to 1.

3. The process according to claim 1, wherein the recycling is carried out at a recycle ratio of the volume of liquid reactor effluent recycled back through the reactor, with respect to the volume of the portion of the liquid reactor effluent that is not recycled, from about 1 to 1 to about 100 to 1.

4. The process according to claim 1, comprising a further step of feeding into a second reactor the portion of the liquid reactor effluent that is not recycled.

5. The process according to claim 4, wherein the second reactor is provided with a solid hydrogenation catalyst and hydrogen gas.

6. The process according to claim 5, comprising a further step of recycling a portion of a liquid reactor effluent exiting the second reactor back through the second reactor.

7. The process according to claim 6, wherein the recycling of a portion of the liquid reactor effluent exiting the second reactor back through the second reactor is carried out at a recycle ratio of the volume of the liquid reactor effluent recycled back through the second reactor, with respect to the volume of the portion of the liquid reactor effluent that is not recycled back through the second reactor, of at least about 1 to 1.

8. The process according to claim 1, wherein the aldol catalyst solution comprises a solution of an alkali- or an alkaline-earth metal hydroxide or alkoxide, wherein the hydroxide or alkoxide is present in the solution in an amount of from about 0.5 to about 50 wt. %.

9. The process according to claim 1, wherein the aldol catalyst solution comprises a solution of an alkali- or an alkaline-earth metal hydroxide or alkoxide, wherein the hydroxide or alkoxide is present in the solution in an amount of from about 2 to about 10 wt. %.

10. The process according to claim 1, wherein the aldol catalyst solution comprises a solution of an alkali- or an alkaline-earth metal hydroxide or alkoxide, wherein the molar ratio of the hydroxide or alkoxide of the alkali metal or alkaline earth metal catalyst to the lower molecular weight aldehyde is from about 0.001:1 to about 0.4:1.

11. The process according to claim 4, wherein the molar ratio of the hydroxide or alkoxide of the alkali metal or alkaline earth metal catalyst to the lower molecular weight aldehyde is from about 0.05:1 to about 0.15:1.

12. The process according to claim 1, wherein the aldol catalyst solution comprises one or more of: sodium hydroxide, potassium hydroxide, cesium hydroxide, lithium hydroxide, magnesium hydroxide, calcium hydroxide, barium hydroxide, sodium methoxide, sodium ethoxide, sodium propoxide, sodium butoxide, potassium methoxide, potassium ethoxide, potassium propoxide, potassium butoxide, cesium methoxide, cesium ethoxide, cesium propoxide, cesium butoxide, lithium methoxide, lithium ethoxide, lithium propoxide, lithium butoxide, magnesium methoxide, magnesium ethoxide, magnesium propoxide, magnesium butoxide, calcium methoxide, calcium ethoxide, calcium propoxide, calcium butoxide, barium methoxide, barium ethoxide, barium propoxide, or barium butoxide.

13. The process according to claim 1, wherein the aldol catalyst solution comprises one or more of: sodium hydroxide or potassium hydroxide.

14. The process according to claim 1, wherein the temperature in the reactor is from about 0° C. to about 200° C.

15. The process according to claim 1, wherein the temperature in the reactor is from about 25° C. to about 175° C.

16. The process according to claim 1, wherein the temperature in the reactor is from about 90° C. to about 130° C.

17. The process according to claim 1, wherein the hydrogen gas is provided at a pressure from about 3 to about 150 bar.

18. The process according to claim 1, wherein the hydrogen gas is provided at a pressure from about 15 to about 30 bar.

19. The process according to claim 1, wherein the residence time of the reaction mixture in the reactor is from about 2 to about 200 minutes.

20. The process according to claim 1, wherein the residence time of the reaction mixture in the reactor is from about 10 to about 60 minutes.

21. The process according to claim 1, wherein the recycle ratio is from about 5:1 to about 30:1.

22. The process according to claim 1, where the hydrogenation catalyst is a shaped or extruded transition metal catalyst supported on a stable support.

23. The process according to claim 1, wherein the hydrogenation catalyst comprises one or more of: Ni, Co, Cu, Cr, Pt, Pd, Rh, Ru, Re, or Ir.

24. The process according to claim 1, wherein the hydrogenation catalyst is supported on a stable support comprising one or more of: alumina, silica, silica-alumina, or carbon.

25. The process according to claim 1, wherein the hydrogenation catalyst comprises palladium on carbon.

26. The process according to claim 1, wherein the hydrogenation catalyst has a metal loading of from about 0.1 to about 90 wt. %.

27. The process according to claim 1, wherein the hydrogenation catalyst has a metal loading of from about 0.1 to about 5 wt. %.

28. The process according to claim 1, wherein the lower molecular weight aldehyde comprises one or more of: acetaldehyde; propionaldehyde; n-butyraldehyde; 2-methyl-propanal; n-pentanal and structural isomers such as 2-methyl-butanal, 3-methyl-butanal, 2,2-dimethyl-propanal; n-hexanal and structural isomers such as 2-ethyl-butanal, 2,2-dimethylbutanal, 2,3-dimethylbutanal, 2-methyl-pentanal, 3-methylpentanal, 4-methyl-pentanal; n-heptanal and structural isomers such as 2-methylhexanal, 2-ethylpentanal, 2,2-dimethylpentanal, 2,3-dimethylpentanal, 2,4-dimethylpentanal, 2-ethyl-3-methylbutanal, 2-ethyl-2-methylbutanal; n-octanal and structural isomers such as 2-ethylhexanal, n-nonanal and structural isomers; cyclopropane carboxaldehyde; cyclobutane carboxaldehyde; cyclopentane carboxaldehyde; cyclohexane carboxaldehyde; 2-methylcyclohexane carboxaldehyde; 3-methylhexane carboxaldehyde; and 4-methylhexane carboxaldehyde.

29. The process according to claim 1, wherein the lower molecular weight ketone comprises one or more of: acetone, 2-butanone, 2-pentanone, and 3-methyl-2-butanone.

30. A process for producing methyl amyl ketone, comprising:

feeding an aldol catalyst solution, n-butyraldehyde, and acetone, through a reactor provided with a solid hydrogenation catalyst and hydrogen gas;

recovering a liquid reactor effluent containing methyl amyl ketone as a reaction product; and recycling a portion of the recovered liquid reactor effluent back through the reactor wherein the recycling is carried out at a recycle ratio of the volume of liquid reactor effluent recycled back through the reactor, with respect to the volume of the portion of the liquid reactor effluent that is not recycled, of at least about 1 to 1.

31. The process according to claim 30, wherein the recycling is carried out at a recycle ratio of the volume of liquid reactor effluent recycled back through the reactor, with respect to the volume of the portion of the liquid reactor effluent that is not recycled, from about 1 to 1 to about 1000 to 1.

32. The process according claim 30, comprising a further step of feeding into a second reactor the portion of the liquid reactor effluent that is not recycled.

33. The process according to claim 28, wherein the second reactor is provided with a solid hydrogenation catalyst and hydrogen gas.

34. The process according to claim 33, comprising a further step of recycling a portion of a liquid reactor effluent exiting the second reactor back through the second reactor, at a recycle ratio of the volume of the liquid reactor effluent recycled back through the second reactor, with respect to the volume of the portion of the liquid reactor effluent that is not recycled back through the second reactor, of at least about 1 to 1.

35. The process according to claim 30, wherein the aldol catalyst solution comprises a solution of an alkali- or an alkaline-earth metal hydroxide or alkoxide, wherein the hydroxide or alkoxide is present in the solution in an amount of from about 0.5 to about 50 wt. %.

36. The process according to claim 30, wherein the aldol catalyst solution comprises a solution of an alkali- or an alkaline-earth metal hydroxide or alkoxide, wherein the molar ratio of the hydroxide or alkoxide of the alkali metal or alkaline earth metal catalyst to n-butyraldehyde is from about 0.001:1 to about 0.4:1.

37. The process according to claim 30, wherein the aldol catalyst solution comprises one or more of: sodium hydroxide or potassium hydroxide.

38. The process according to claim 30, wherein the temperature in the reactor is from about 0° C. to about 200° C.

39. The process according to claim 30, wherein the hydrogen gas is provided at a pressure from about 3 to about 150 bar.

40. The process according to claim 30, wherein the residence time of the reaction mixture in the reactor is from about 2 to about 200 minutes.

41. The process according to claim 31, wherein the recycle ratio is from about 1:1 to about 1000:1.

42. The process according to claim 30, where the hydrogenation catalyst is a shaped or extruded transition metal catalyst supported on a stable support.

43. The process according to claim 30, wherein the hydrogenation catalyst comprises one or more of: Ni, Co, Cu, Cr, Pt, Pd, Rh, Ru, Re, or Ir.

44. The process according to claim 30, wherein the hydrogenation catalyst is supported on a stable support comprising one or more of: alumina, silica, silica-alumina, or carbon.

45. The process according to claim 30, wherein the hydrogenation catalyst comprises palladium on carbon.

46. A process for producing methyl isoamyl ketone, comprising:

feeding an aldol catalyst solution, i-butyraldehyde, and acetone, through a reactor provided with a solid hydrogenation catalyst and hydrogen gas;

recovering a liquid reactor effluent containing methyl isoamyl ketone as a reaction product; and recycling a portion of the recovered liquid reactor effluent back through the reactor wherein the recycling is carried out at a recycle ratio of the volume of liquid reactor effluent recycled back through the reactor, with respect to the volume of the portion of the liquid reactor effluent that is not recycled, of at least about 1 to 1.

47. The process according to claim 46, wherein the recycling is carried out at a recycle ratio of the volume of liquid reactor effluent recycled back through the reactor, with respect to the volume of the portion of the liquid reactor effluent that is not recycled, from about 1 to 1 to about 1000 to 1.

48. The process according to claim 46, comprising a further step of feeding into a second reactor the portion of the liquid reactor effluent that is not recycled.

49. The process according to claim 48, wherein the second reactor is provided with a solid hydrogenation catalyst and hydrogen gas.

50. The process according to claim 49, comprising a further step of recycling a portion of a liquid reactor effluent exiting the second reactor back through the second reactor, at a recycle ratio of the volume of the liquid reactor effluent recycled back through the second reactor, with respect to the volume of the portion of the liquid reactor effluent that is not recycled back through the second reactor, of at least about 1 to 1.

51. The process according to claim 46, wherein the aldol catalyst solution comprises a solution of an alkali- or an alkaline-earth metal hydroxide or alkoxide, wherein the hydroxide or alkoxide is present in the solution in an amount of from about 0.5 to about 50 wt. %.

52. The process according to claim 46, wherein the aldol catalyst solution comprises a solution of an alkali- or an alkaline-earth metal hydroxide or alkoxide, wherein the molar ratio of the hydroxide or alkoxide of the alkali metal or alkaline earth metal catalyst to the i-butyraldehyde is from about 0.001:1 to about 0.4:1.

53. The process according to claim 46, wherein the aldol catalyst solution comprises one or more of: sodium hydroxide or potassium hydroxide.

54. The process according to claim 46, wherein the temperature in the reactor is from about 0° C. to about 200° C.

55. The process according to claim 46, wherein the hydrogen gas is provided at a pressure from about 3 to about 150 bar.

56. The process according to claim 46, wherein the residence time of the reaction mixture in the reactor is from about 2 to about 200 minutes.

57. The process according to claim 47, wherein the recycle ratio is from about 1:1 to about 1000:1.

58. The process according to claim 46, where the hydrogenation catalyst is a shaped or extruded transition metal catalyst supported on a stable support.

59. The process according to claim 46, wherein the hydrogenation catalyst comprises one or more of: Ni, Co, Cu, Cr, Pt, Pd, Rh, Ru, Re, or Ir.

60. The process according to claim 46, wherein the hydrogenation catalyst is supported on a stable support comprising one or more of: alumina, silica, silica-alumina, or carbon.

61. The process according to claim 46, wherein the hydrogenation catalyst comprises palladium on carbon.

62. A process for producing methyl propyl ketone, comprising:

feeding an aldol catalyst solution, acetaldehyde, and acetone, through a reactor provided with a solid hydrogenation catalyst and hydrogen gas;

recovering a liquid reactor effluent containing methyl propyl ketone as a reaction product; and recycling a portion of the recovered liquid reactor effluent back through the reactor wherein the recycling is carried out at a recycle ratio of the volume of liquid reactor effluent recycled back through the reactor, with respect to the volume of the portion of the liquid reactor effluent that is not recycled, of at least about 1 to 1.

63. The process according to claim 62, wherein the recycling is carried out at a recycle ratio of the volume of liquid reactor effluent recycled back through the reactor, with respect to the volume of the portion of the liquid reactor effluent that is not recycled, from about 1 to 1 to about 1000 to 1.

64. The process according to claim 62, comprising a further step of feeding into a second reactor the portion of the liquid reactor effluent that is not recycled.

65. The process according to claim 64, wherein the second reactor is provided with a solid hydrogenation catalyst and hydrogen gas.

66. The process according to claim 65, comprising a further step of recycling a portion of a liquid reactor effluent exiting the second reactor back through the second reactor, at a recycle ratio of the volume of the liquid reactor effluent recycled back through the second reactor, with respect to the volume of the portion of the liquid reactor effluent that is not recycled back through the second reactor, of at least about 1 to 1.

67. The process according to claim 62, wherein the aldol catalyst solution comprises a solution of an alkali- or an alkaline-earth metal hydroxide or alkoxide, wherein the hydroxide or alkoxide is present in the solution in an amount of from about 0.5 to about 50 wt. %.

68. The process according to claim 62, wherein the aldol catalyst solution comprises a solution of an alkali- or an alkaline-earth metal hydroxide or alkoxide, wherein the molar ratio of the hydroxide or alkoxide of the alkali metal or alkaline earth metal catalyst to acetaldehyde is from about 0.001:1 to about 0.4:1.

69. The process according to claim 62, wherein the aldol catalyst solution comprises one or more of: sodium hydroxide or potassium hydroxide.

70. The process according to claim 62, wherein the temperature in the reactor is from about 0° C. to about 200° C.

71. The process according to claim 62, wherein the hydrogen gas is provided at a pressure from about 3 to about 150 bar.

72. The process according to claim 62, wherein the residence time of the reaction mixture in the reactor is from about 2 to about 200 minutes.

73. The process according to claim 62, where the hydrogenation catalyst is a shaped or extruded transition metal catalyst supported on a stable support.

74. The process according to claim 62, wherein the hydrogenation catalyst comprises one or more of: Ni, Co, Cu, Cr, Pt, Pd, Rh, Ru, Re, or Ir.

75. The process according to claim 62, wherein the hydrogenation catalyst is supported on a stable support comprising one or more of: alumina, silica, silica-alumina, or carbon.

76. The process according to claim 62, wherein the hydrogenation catalyst comprises palladium on carbon.

* * * * *